United States Patent
Doane et al.

[11] Patent Number: 6,004,519
[45] Date of Patent: Dec. 21, 1999

[54] ALUMINUM PROMOTED HYDROGENATION OF ALKYLATION SLUDGE FOR ALUMINUM CHLORIDE RECOVERY

[75] Inventors: Elliott P. Doane, Oklahoma City, Okla.; Jim Yuen-Fong Low, Missouri City, Tex.; Larry G. Sherman; William A. Yuill, both of Edmond, Okla.

[73] Assignee: Kerr-McGee Corporation, Oklahoma City, Okla.

[21] Appl. No.: 08/775,522

[22] Filed: Jan. 2, 1997

Related U.S. Application Data

[63] Continuation-in-part of application No. 08/370,056, Jan. 9, 1995, Pat. No. 5,593,569.

[51] Int. Cl.$^6$ ............................................. C01F 7/56
[52] U.S. Cl. ........................ 423/111; 423/122; 423/123; 423/124; 423/495; 208/13
[58] Field of Search ..................... 423/123, 124, 423/130, 495, 122, 111, 127; 208/13

[56] References Cited

U.S. PATENT DOCUMENTS

| | | | |
|---|---|---|---|
| 1,405,734 | 2/1922 | McAfee | 423/130 |
| 1,582,131 | 4/1926 | Danner | 423/130 |
| 2,211,207 | 8/1940 | Ipatieff et al. | 502/225 |
| 2,348,701 | 5/1944 | Schmerling | 423/130 |
| 2,416,049 | 2/1947 | Foster | 423/130 |
| 2,517,692 | 8/1950 | Mavity | 423/123 |
| 2,843,455 | 7/1958 | Pardee | 423/495 |
| 3,476,825 | 11/1969 | Hutson, Jr. et al. | 585/253 |
| 3,554,695 | 1/1971 | Marshall et al. | 423/130 |
| 3,846,334 | 11/1974 | Di Fiore et al. | 502/32 |
| 4,017,584 | 4/1977 | Messina et al. | 423/495 |

FOREIGN PATENT DOCUMENTS 0 157 339  10/1985  European Pat. Off. .................. 208/13

*Primary Examiner*—Ngoc-Yen Nguyen
*Attorney, Agent, or Firm*—Herbert M. Hanegan; Charles L. Warner II; J. Rodgers Lunsford III

[57] ABSTRACT

The recovery of aluminum chloride from deactivated alkylation catalyst complexes by hydrogenation using hydrogen gas and an aluminum catalyst is disclosed. Using aluminum to catalyze the hydrogenation allows the reaction to proceed at a lower temperature and pressure while reducing the amount of hydrogen chloride present in the reactor thus reducing the corrosiveness and cost of the aluminum chloride recovery. Methods for batch, batchwise continuous, and continuous aluminum chloride recovery are disclosed.

32 Claims, 1 Drawing Sheet

ALKYLATOR AND CATALYST RECOVERY UNIT

ALKYLATOR AND CATALYST RECOVERY UNIT

ALUMINUM PROMOTED HYDROGENATION OF ALKYLATION SLUDGE FOR ALUMINUM CHLORIDE RECOVERY

CROSS-REFERENCE TO RELATED APPLICATION

This is a continuation-in-pate of co-pending application Ser. No. 08/370,056, filed Jan. 9, 1995, now U.S. Pat. No. 5,593,569.

BACKGROUND OF THE INVENTION

1. Field of the Invention

The present invention relates to batch, batchwise-continuous, and continuous processes for recovering aluminum chloride from deactivated alkylation catalyst complexes by low-corrosion hydrogenation using an aluminum catalyst. Most specifically, the present invention relates to the hydrogenation of a complex sludge of aluminum chloride and olefinic hydrocarbon compounds using an aluminum powder catalyst in the presence of hydrogen gas; the aluminum powder also acting as a reagent to remove hydrochloric acid from the reaction mixture to reduce the corrosiveness and cost of the hydrogenation step.

2. Description of the Prior Art

The use of aluminum chloride based homogeneous complexes to catalyze hydrocarbon conversion reactions such as alkylation and isomerization is known in the art. Alkylation processes for the production of gasoline that use a soluble alkylaluminum chloride—based catalyst, such as the catalyst and process disclosed in U.S. patent application Ser. No. 08/370,056 by Sherman, now U.S. Pat. No. 5,593,569, have been shown to be more cost effective and environmentally friendly than conventional sulfuric acid and hydrofluoric acid alkylation processes. As the alkylation reaction in such processes approaches completion, the homogeneous catalyst degrades to a less active state and forms a separate sludge phase. The present invention is directed to the recovery of aluminum chloride from this sludge for recycle to produce the soluble catalyst.

Aluminum chloride can be recovered by hydrogenation of the sludge at high temperature (200° C.) and high pressure (3000 psig), but the combination of aluminum chloride and hydrochloric acid produced during hydrogenation is very corrosive at high temperatures for a carbon-steel reactor, making the hydrogenation step expensive. The corrosion rate can be reduced by reducing the temperature and pressure or by reducing the amount of hydrochloric acid present. While rhodium or palladium, both well-known hydrogenation catalysts, can be used to lower temperature and pressure, these catalysts are expensive. It has now been found that metallic aluminum (a less expensive agent) is an effective hydrogenation catalyst in the presence of hydrogen gas for these homogeneous, high bound-hydrocarbon content, alkylaluminum chloride—based catalysts and promotes the liberation of aluminum chloride and paraffinic by-products at a lower temperature (150° C.) and pressure (1500 psig) than non-catalytic hydrogenation. The metallic aluminum also scavenges excess hydrochloric acid utilized in allylation or produced in the hydrogenation process, thereby greatly reducing reactor corrosion.

The prior art contains numerous methods for recovering spent catalysts from alkylation processes but none using aluminum to catalyze the hydrogenation of alkyaluminum chloride—based catalysts. For example, U.S. Pat. No. 2,517,692 teaches the regeneration of deactivated aluminum halide catalysts from sludge utilizing hydrochloric acid in conjunction with an olefin and aluminum as a reagent. Hydrogenation is not practiced and the aluminum is sacrificial, reacting with hydrochloric acid to produce more aluminum chloride. The process is non-catalytic and is a net producer of aluminum chloride relative to the present invention. Similarly, U.S. Pat. No. 3,846,334 deals with regeneration of sludge to produce a "reactivated complex," not aluminum chloride, using aluminum with hydrochloric acid and benzene, not hydrogen. The present invention regenerates aluminum chloride using hydrogenation and no aromatic hydrocarbon reagents. Also, U.S. Pat. No. 3,476,825 teaches the use of aluminum powder and hydrochloric acid to produce aluminum chloride in-situ, not to regenerate catalyst from a sludge. In a separate step, hydrogen was used to regenerate the catalyst but not in the presence of aluminum.

Further examples include U.S. Pat. No. 4,017,584 which uses aluminum that has been pretreated with hydrogen chloride to disproportionate the aluminum chloride from the sludge complex at temperatures not exceeding 100° C. Unlike the present invention which practices catalytic hydrogenation, no hydrogen is used. Also the aluminum is stoichiometrically consumed in the reaction. For every three moles of aluminum chloride released from the sludge, one mole of aluminum is converted to aluminum chloride. In the present invention, aluminum is catalytic in the hydrogenation step and is only consumed by reaction with any net excess hydrochloric acid in the system resulting from the presence of more than stoichiometric amounts of alkylation catalyst complex activator which is also liberated during hydrogenation. The method taught by the '584 patent did not produce aluminum chloride when applied to the high-hydrocarbon (about 46 weight % hydrocarbon) alkyaluminum chloride—based catalysts that are the focus of the present invention. U.S. Pat. No. 1,582,131 discloses non-catalytic hydrogenation of aluminum chloride catalyst residues with the recovery of aluminum chloride by distillation. U.S. Pat. No. 2,211,207 describes hydrogenation in the presence of heavy metal halides, it does not teach the utility of aluminum as a catalyst for aluminum chloride recovery.

None of the aforementioned patents teaches the use of aluminum powder as the hydrogenation catalyst for aluminum chloride recovery which is the subject of this application.

SUMMARY OF THE INVENTION

According to the present invention, a batch process for recovering aluminum chloride from an alkylaluminum chloride—based catalyst sludge comprises mixing said sludge with metallic aluminum in the presence of hydrogen at a pressure of 1500 psig or below and at a temperature of 200° C. or below for about four hours or less. The present invention also encompasses a batchwise-continuous and a continuous process for recovering aluminum chloride from an alkylaluminum chloride - based catalyst sludge both comprising mixing said sludge with metallic aluminum, isobutane, and hydrogen gas in a hydrogenation zone at a pressure of 1500 psig or below and at a temperature of 200° C. or below.

DESCRIPTION OF THE PREFERRED EMBODIMENTS

Figure 1:
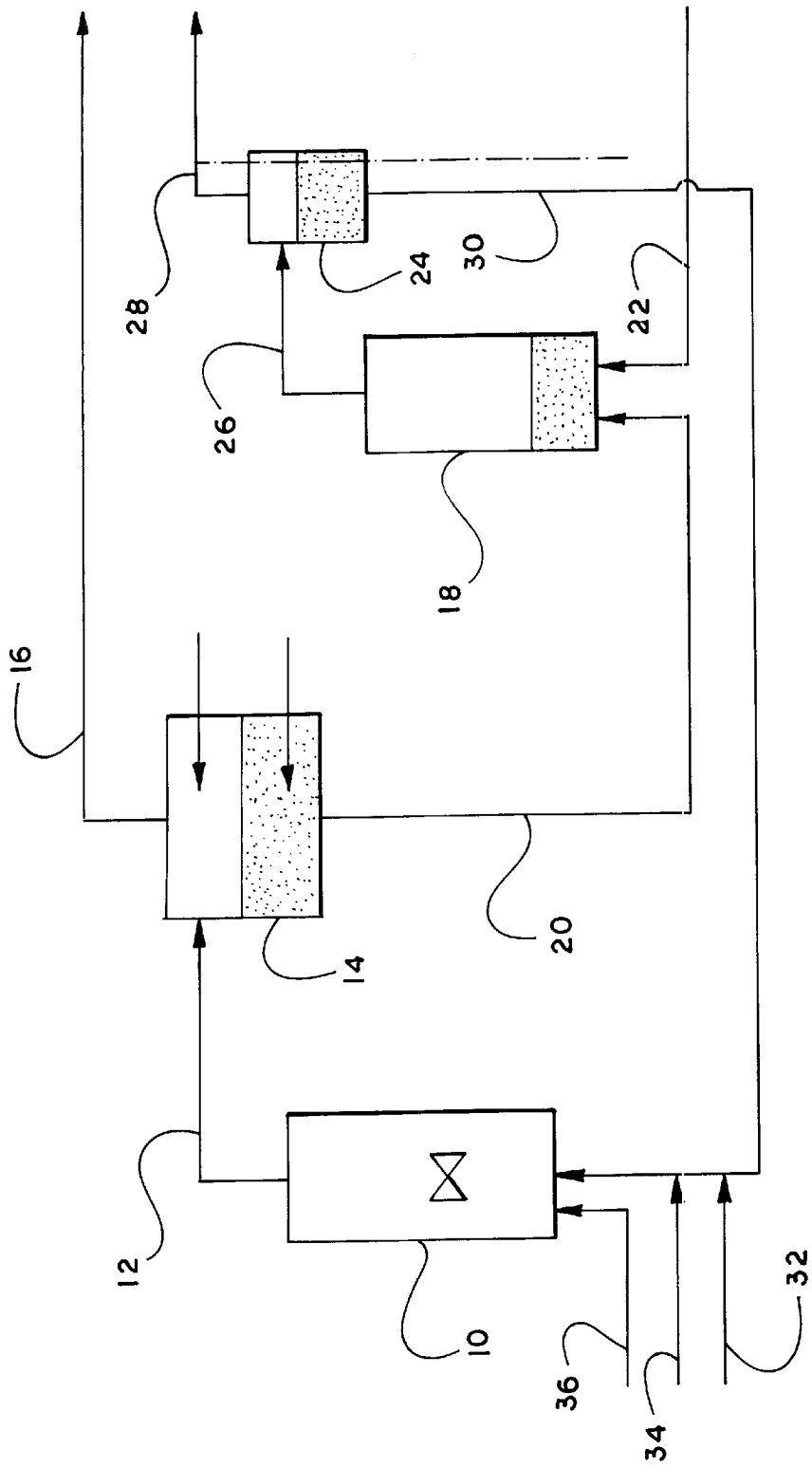
FIG. 1 is a schematic representation of one embodiment of the present invention.

Shown in FIG. 1 is a schematic for the batchwise-continuous and continuous aluminum chloride recovery processes of the present invention for use in a olefin alkylation process for fuels. In general, the process comprises: an alkylation unit 10 from which alkylate, isobutane, and sludge complex from the alkylation process are passed by way of a flowline 12 into a settling tank 14, which is adapted to discharge the alkylate and isobutane by way of a flowline 16 for further processing outside the scope of this invention, and to pass the sludge complex into a hydrogenation unit 18 by way of a flowline 20 for reacting with hydrogen gas, which is passed into the hydrogenation unit with isobutane by way of a flowline 22, and catalytic aluminum which is resident in the hydrogenation unit 18 and is replenished in discrete intervals as needed. As the hydrogenation reaction proceeds and aluminum chloride is liberated from the sludge complex, said aluminum chloride dissolves in said isobutane and is passed from the hydrogenation unit by way of a flowline 26 into a separation unit 24 in which hydrogen gas is discharged by way of a flowline 28 for further processing outside the scope of this invention, and the aluminum chloride-containing isobutane stream is returned to the alkylation unit 10 by way of a flowline 30 into which additional isobutane from a flowline 32, and alkylation catalyst activator from a flowline 34, are added and complex with said aluminum chloride to form a homogeneous, high bound-hydrocarbon, alkylaluminum chloride-based catalyst prior to entry into the alkylation unit for use in the alkylation process with olefin introduced to the alkylation unit by way of a flowline 36.

The present invention relates to batch, batchwise-continuous, and continuous processes for recovering aluminum chloride from homogeneous, high bound-hydrocarbon, alkylaluminum chloride—based catalyst sludge using aluminum—catalyzed hydrogenation. The alkylation catalyst to which this invention is directed is formed by reaction of aluminum chloride, which is the catalyst precursor, with a paraffin. A promoter is then added. Advantageously, the paraffin is isobutane and the promoter is 1-chlorobutane, although any light paraffin containing a tertiary carbon will work in this system. Unlike conventional aluminum chloride based alkylation catalysts of the art which tend to have low "bound-hydrocarbon" levels (from about 16 to about 36 weight percent bound-hydrocarbon) relative to "bound-aluminum chloride" levels (from about 64 to about 84 weight percent bound-aluminum chloride), the catalyst which forms the sludge complex for the present invention has a relatively high bound-hydrocarbon level (from about 43 to about 70 weight percent, usually about 50 weight percent bound-hydrocarbon, preferably said homogeneous aluminum chloride-based catalyst comprises about 46 weight percent bound-hydrocarbon and about 54 weight percent bound-aluminum chloride. Advantageously the recovery rate of the aluminum chloride from the sludge complex is from about 2 to about 3 weight sludge complex/hour/weight of catalytic aluminum). It is believed that this compositional difference is the primary reason the catalyst recovery method disclosed in U.S. Pat. No. 4,017,584 was not effective in separating aluminum chloride from this sludge complex.

According to U.S. patent application Ser. No. 08/093,463, the homogeneous, high bound-hydrocarbon content, alkylaluminum chloride—based catalyst disclosed therein is effective, even at low acid concentrations, in alkylating 2-butene and other olefins such as propylene, 1-butene, and 2-pentene, with isobutane to produce a preponderance of high-octane iso-paraffins. As the catalyst ages it becomes a sludge complex that is not soluble in paraffins such as isobutane or typical alkylate. Consequently, it precipitates when it is allowed to remain quiescent in a settling tank and can be gravity separated from the hydrocarbon phase of the alkylation process and then transferred to a hydrogenation unit for treatment with the process of this invention. Advantageously, the hydrogenation unit is a stirred reactor for either the batch, the batchwise-continuous, or the continuous process. Agitation, by means of stirring or induced turbulence, facilitates contact between the catalyst, the hydrogen, and the sludge complex and transports heat away from the catalyst to avoid "hot spots" and a runaway reaction. Agitation in the batchwise-continuous and continuous processes can be promoted by the introduction of the isobutane/hydrogen gas stream into the hydrogenation unit.

The aluminum catalyst for the hydrogenation process should be relatively pure, advantageously 99% pure, to avoid generation of other metal chlorides which could then be introduced to the alkylation system with the recycled aluminum chloride catalyst. The form of the catalyst should present the maximum surface per weight. In a stirred reactor, effective forms of aluminum include powder and gauze, preferably powder.

In a batch process, the present invention advantageously comprises the steps of:

a. mixng sludge complex with aluminum in a ratio of from about 6:1 to about 7:1;

b. said mixing taking place in the presence of between about 500 psig and about 1500 psig of hydrogen gas;

c. at a temperature of between about 125° C. and about 200° C.;

d. for between about 2 and about 4 hours;

e. then allowing reactants to cool to precipitate aluminum chloride.

Preferably, the sludge complex—aluminum catalyst mixture in step (a) is in a ratio of about 6:1. Preferably, the aluminum catalyst is in powder form. Advantageously, the hydrogen gas in step (b) is at a pressure of from about 1000 psig to about 1500 psig. Preferably the hydrogen gas in step (b) is at a pressure of about 1500 psig. Hydrogen gas can be fed continuously to the reactor or hydrogen pressure can be maintained manually with no hydrogen exiting the reactor. Advantageously, the reaction temperature in step (c) is from about 140° C. to about 180° C. Preferably the reaction temperature in step (c) is about 150° C. Preferably, the reaction time in step (d) is about 3 hours.

In a batchwise-continuous process, the present invention advantageously comprises the steps of:

a. passing alkylate, isobutane, and sludge complex from an alkylation zone to a settling tank and allowing the sludge complex to settle from the alkylate;

b. transferring sludge complex from the settling tank to a hydrogenation zone at set intervals;

c. contacting the sludge complex with catalytic aluminum in the presence of between about 500 psig and 1500 psig of hydrogen gas and isobutane;

d. at a temperature of between about 125° C. and about 200° C.

e. for between about 2 and about 4 hours;

f. thus forming aluminum chloride;

g. continuously dissolving the aluminum chloride in said isobutane; and h. discharging the aluminum chloride-isobutane solution from the hydrogenation zone for recycle to the alkylation zone.

Preferably the catalytic aluminum is in powder or mesh form. Advantageously, the hydrogen gas in step (c) is at a pressure of from about 1000 psig to about 1500 psig. Preferably, the hydrogen gas in step (c) is at a pressure of about 1500 psig. Advantageously, the reaction temperature in step (d) is from about 140° C. to about 180° C. Preferably, the reaction temperature in step (d) is about 150° C. Preferably the reaction time in step (e) is about 3 hours. Preferably, agitation for the reaction is provided by stirring the isobutane, the sludge complex, and catalytic aluminum in the hydrogenation zone.

In a continuous process, the present invention advantageously comprises the steps of:
  a. passing alkylate, isobutate, and sludge complex from an alkylation zone to a settling tank and allowing the sludge complex to settle from the alkylate;
  b. continuously transferring sludge complex from the settling tank to a hydrogenation zone;
  c. contacting the sludge complex with catalytic aluminum in the presence of between about 500 psig and 1500 psig of hydrogen gas and isobutane;
  d. at a temperature of between about 125° C. and about 200° C.;
  e. thus forming aluminum chloride;
  f. continuously dissolving the aluminum chloride in said isobutane; and
  g. discharging the aluminum chloride-isobutane solution from the hydrogenation zone for recycle to the alkylation zone.

Preferably the catalytic aluminum is in powder or mesh form. Advantageously, the hydrogen gas in step (b) is at a pressure of from about 1000 psig to about 1500 psig. Preferably, the hydrogen gas in step (b) is at a pressure of about 1500 psig. Advantageously, the reaction temperature in step (c) is from about 140° C. to about 180° C. Preferably, the reaction temperature in step (c) is about 150° C. Preferably, agitation for the reaction is provided by stirring the isobutane, the sludge complex, and catalytic aluminum in the hydrogenation zone.

The products of sludge complex hydrogenation are aluminum chloride and paraffinic hydrocarbons. After the aluminum chloride is liberated from the sludge complex in a continuous process, it is dissolved in isobutane and is transferred out of the hydrogenation reactor, it is then mixed with an activator such as 1-chlorobutane and additional isobutane to form the active catalyst, and fed back into the alkylator to produce more alkylate. Using the process of the present invention, aluminum chloride recoveries approach 100% because the sludge complex is insoluble and will remain in the hydrogenation reactor until all of the aluminum chloride has been removed. Catalysts made with recycled aluminum chloride are as effective in producing high research octane number (RON) altylates as are catalysts formed using fresh commercial aluminum chloride. RONs above 94 can be achieved with both catalysts.

EXAMPLE 1

This example deals with a batch, aluminum catalyzed, sludge complex hydrogenation. The procedure was carried out in a 35 mL Parr stirred autoclave reactor. A mixture of 18 g of sludge complex and 3 grams of aluminum powder was placed in the reactor and heated to 150° C. in the presence of 1500 psig of hydrogen for three hours with stirring (700 rpm). The reactor was allowed to cool to ambient temperature overnight. After cooling the mixture, the sludge (a brown liquid) was found to be totally converted to white crystals entrained with some liquid. The crystals were identified to be aluminum chloride by infrared spectra and aluminum and chloride analyses. The aluminum and chloride analysis results are given below.

| Element | Recovered Solid, Wt % | Pure AlCl3, Calculated Value, Wt % |
|---|---|---|
| Aluminum Content | 20.6 | 20.3 |
| Chloride Content | 78.0 | 80.0 |

What is claimed is:

1. A process for the recovery of aluminum chloride from a sludge complex precipitated from the products of an alkylation reaction of an olefin with isobutane promoted by a homogeneous alkylaluminum chloride-based catalyst comprising:
  forming a mixture consisting of the sludge complex and an aluminum catalyst;
  reacting the sludge complex in the mixture with hydrogen in the presence of the aluminum catalyst to form aluminum chloride; and recovering the aluminum chloride from the reaction mixture, wherein the reaction step is carried out for a time of from about 2 to about 4 hours and the sludge complex and the aluminum catalyst are mixed in a weight ratio of from about 6:1 to about 7:1.

2. The process of claim 1 wherein the reaction step is carried out for a time of about 3 hours and the sludge complex and the aluminum catalyst are mixed in a weight ratio of about 6:1.

3. The process of claim 1 wherein the homogeneous alkylaluminum chloride-based catalyst comprises from about 43 weight percent bound-hydrocarbon to about 70 weight percent bound-hydrocarbon and from about 30 weight percent bound-aluminum chloride to about 57 weight percent bound-aluminum chloride.

4. The process of claim 3 wherein hydrogenis provided in the gaseous state at a pressure of from about 500 psig to about 1500 psig.

5. The process of claim 4 wherein hydrogen gas is present at a pressure of from about 1000 psig to about 1500 psig.

6. The process of claim 5 wherein hydrogen gas is present at a pressure of about 1500 psig.

7. The process of claim 4 wherein the aluminum chloride is recovered by dissolving in isobutane.

8. The process of claim 4 wherein the aluminum chloride is recovered by allowing said reaction mixture to cool and the aluminum chloride to precipitate.

9. The process of claim 4 wherein said aluminum catalyst is at least 99% pure aluminum.

10. The process of claim 4 including the step of constantly agitating the reactants in the presence of the aluminum catalyst.

11. The process of claim 4 wherein the reaction step is carried out at a temperature of from about 125° C. to about 200° C.

12. The process of claim 11 including the step of constantly agitating the reactants in the presence of the aluminum catalyst during the time they are heated.

13. The process of claim 11wherein the reaction temperature is from about 140° C. to about 180° C.

14. The process of claim 13 wherein the reaction temperature is about 150° C.

15. The process of claim 13 performed as a batch process.

16. The process of claim 13 performed as a continuous process.

17. The process of claim 13 performed as a batch-wise continuous process.

18. The process of claim 16 including the steps of:

passing alkylate, isobutane and sludge complex from an alkylation zone to a settling tank and allowing the sludge complex to settle from the alkylate and isobutane; continuously transferring the sludge complex from said settling tank to a hydrogenation zone;

contacting said sludge complex with hydrogen gas in the presence of an aluminum catalyst and isobutane;

forming aluminum chloride and simultaneously dissolving the aluminum chloride in the isobutane; and discharging the aluminum chloride-isobutane solution from said hydrogenation zone.

19. The process of claim 18 wherein the contacting rate in the hydrogenation zone is from about 2 to about 3 weight of sludge complex/hour/weight of aluminum catalyst.

20. The process of claim 18 including the step of recycling the aluminum chloride-isobutane solution to said alkylation zone.

21. The process of claim 18 wherein the aluminum catalyst is in a mesh form.

22. The process of claim 18 including the step of constantly agitating the reactants in the presence of the aluminum catalyst in the hydrogenation zone.

23. The process of claim 17 including the steps of:

passing alkylate, isobutane and sludge complex from an alkylation zone to a settling tank and allowing the sludge complex to settle from the alkylate and isobutane;

transferring the sludge complex from said settling tank to a hydrogenation zone at periodic time intervals;

contacting said sludge complex with hydrogen as in the presence of an aluminum catalyst and isobutane;

forming aluminum chloride and simultaneously dissolving the aluminum chloride in the isobutane; and discharging the aluminum chloride-isobutane solution from said hydrogenation zone.

24. The process of claim 23 including the step of recycling the aluminum chloride-isobutane solution to said alkylation zone.

25. The process of claim 23 wherein the aluminum catalyst is in a mesh form.

26. The process of claim 23 including the step of constantly agitating the reactants in the presence of the aluminum catalyst in the hydrogenation zone.

27. A process for the recovery of aluminum chloride from a sludge complex precipitated from the products of a hydrocracking reaction conducted in a specified paraffin solvent and promoted by a homogeneous alkylaluminum chloride-based catalyst comprising:

forming a mixture consisting of the sludge complex and an aluminum catalyst;

reacting the sludge complex in the mixture with hydrogen in the presence of the aluminum catalyst to form aluminum chloride; and recovering the aluminum chloride from the reaction mixture, wherein the reaction step is carried out for a time of from about 2 to about 4 hours and the sludge complex and the aluminum catalyst are mixed in a weight ratio of from about 6:1 to about 7:1.

28. The process of claim 27 wherein hydrogen is provided in the gaseous state at a pressure of from about 500 psig to about 1500 psig.

29. The process of claim 27 wherein the reaction step is carried out at a temperature of from about 125° C. to about 200° C.

30. The process of claim 27 wherein said homogeneous alkylaluminum chloride-based catalyst comprises from about 43 weight percent bound-hydrocarbon to about 70 weight percent bound-hydrocarbon and from about 30 weight percent bound-aluminum chloride to about 57 weight percent bound-aluminum chloride.

31. A process for the recovery of aluminum chloride from a sludge complex precipitated from the products of an alkylation reaction of an olefin wit isobutane promoted by a homogeneous alkylaluminum chloride-based catalyst comprising:

forming a mixture consisting of the sludge complex and an aluminum catalyst;

reacting the sludge complex in the mixture with hydrogen in the presence ofthe aluminum catalyst to form aluminum chloride; and recovering the aluminum chloride from the reaction mixture, wherein the homogeneous alkyaluminum chloride-based catalyst comprises from about 43 weight percent bound-hydrocarbon to about 70 weight percent bound-hydrocarbon and from about 30 weight percent bound-aluminum chloride to about 57 weight percent bound-aluminum chloride.

32. A process for the recovery of aluminum chloride from a sludge complex precipitated from the products of a hydrocracking reaction conducted in a paraffinic solvent and promoted by a homogeneous alkylaluminum chloride based catalyst comprising:

forming a mixture consisting ofthe sludge complex and an aluminum catalyst;

reacting the sludge complex in the mixture with hydrogen in the presence of the aluminum catalyst to form aluminum chloride; and recovering the aluminum chloride from the reaction mixture, wherein said homogeneous alkylaluminum chloride-based catalyst comprises from about 43 weight percent bound-hydrocarbon to about 70 weight percent bound-hydrocarbon and from about 30 weight percent bound-aluminum chloride to about 57 weight percent bound-aluminum chloride.

* * * * *

UNITED STATES PATENT AND TRADEMARK OFFICE
CERTIFICATE OF CORRECTION

PATENT NO. : 6,004,519
DATED : December 21, 1999
INVENTOR(S) : Elliott P. Doane et al.

It is certified that error appears in the above-identified patent and that said Letters Patent is hereby corrected as shown below:

Column 6, line 36 (line 1 of claim 4), delete "hydrogenis" and substitute --hydrogen is-- therefor;

Column 7, line 31 (line 8 of claim 23), delete "as" and substitute --gas-- therefor;

Column 7, line 49 (line 3 of claim 27), delete "specified";

Column 7, line 49 (line 3 of claim 27), delete "paraffin" and substitute --paraffinic-- therefor;

Column 8, line 21 (line 3 of claim 31) delete "wit" and substitute --with-- therefor;

Column 8, line 27 (line 9 of claim 31), delete "ofthe" and substitute --of the-- therefor;

Column 8, line 40 (line 4 of claim 32), delete "chloride based" and substitute --chloride-based-- therefor; and Column 8, line 42 (line 6 of claim 32), delete "ofthe" and substitute --of the-- therefor.

Signed and Sealed this

Twenty-sixth Day of September, 2000

Attest:

Q. TODD DICKINSON

*Attesting Officer*  *Director of Patents and Trademarks*